(12) United States Patent
Schaefer

(10) Patent No.: US 6,473,918 B2
(45) Date of Patent: Nov. 5, 2002

(54) CARRIER FOR MEDICAL FACILITIES WITH A LARGE DISPLACEMENT RANGE

(75) Inventor: Danny Genius Aldegonda Schaefer, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 76 days.

(21) Appl. No.: 09/732,588

(22) Filed: Dec. 8, 2000

(65) Prior Publication Data

US 2001/0003218 A1 Jun. 14, 2001

(30) Foreign Application Priority Data

Dec. 8, 1999 (EP) .............................................. 99204198

(51) Int. Cl.[7] .............................................. A61G 13/00
(52) U.S. Cl. ........................................... 5/60 D; 5/601
(58) Field of Search ...................... 5/600, 601; 238/122, 238/123, 134; 600/9

(56) References Cited

U.S. PATENT DOCUMENTS

| | | | | | |
|---|---|---|---|---|---|
| 2,841,714 | A | * | 7/1958 | Vaughn | 378/115 |
| 4,681,308 | A | * | 7/1987 | Rice | 378/209 |
| 5,013,018 | A | * | 5/1991 | Sicek et al. | 378/209 |
| 5,020,089 | A | * | 5/1991 | Cramer et al. | 378/195 |
| 5,210,893 | A | * | 5/1993 | Uosaki et al. | 5/600 |
| 6,094,760 | A | * | 8/2000 | Nonaka et al. | 5/600 |

FOREIGN PATENT DOCUMENTS

DE 3615633 11/1987 ............ A61B/6/00

* cited by examiner

Primary Examiner—Heather Shackelford
Assistant Examiner—Fredrick Conley
(74) Attorney, Agent, or Firm—John Vodopia

(57) ABSTRACT

Carriers for medical facilities, in particular patient tables, sometimes require a large range of displacement. This situation occurs, for example, in interventional MRI where a patient is to be transferred from an operating table to an MRI table which is situated at some distance therefrom. Components of the table may not form obstacles on the floor of the room and the stiffness and stability of the table construction must be maintained. A carrier for medical facilities includes two adjacent box-shaped spaces provided in the floor of the treatment room, said spaces being separated by a partition. One space accommodates only two rails which carry the pedestal of the table but no other components of the displacement mechanism for the table. The other space contains the further components of the displacement mechanism. A guide member protrudes through the partition, via a sealing device so as to guide the movement of the table.

7 Claims, 4 Drawing Sheets

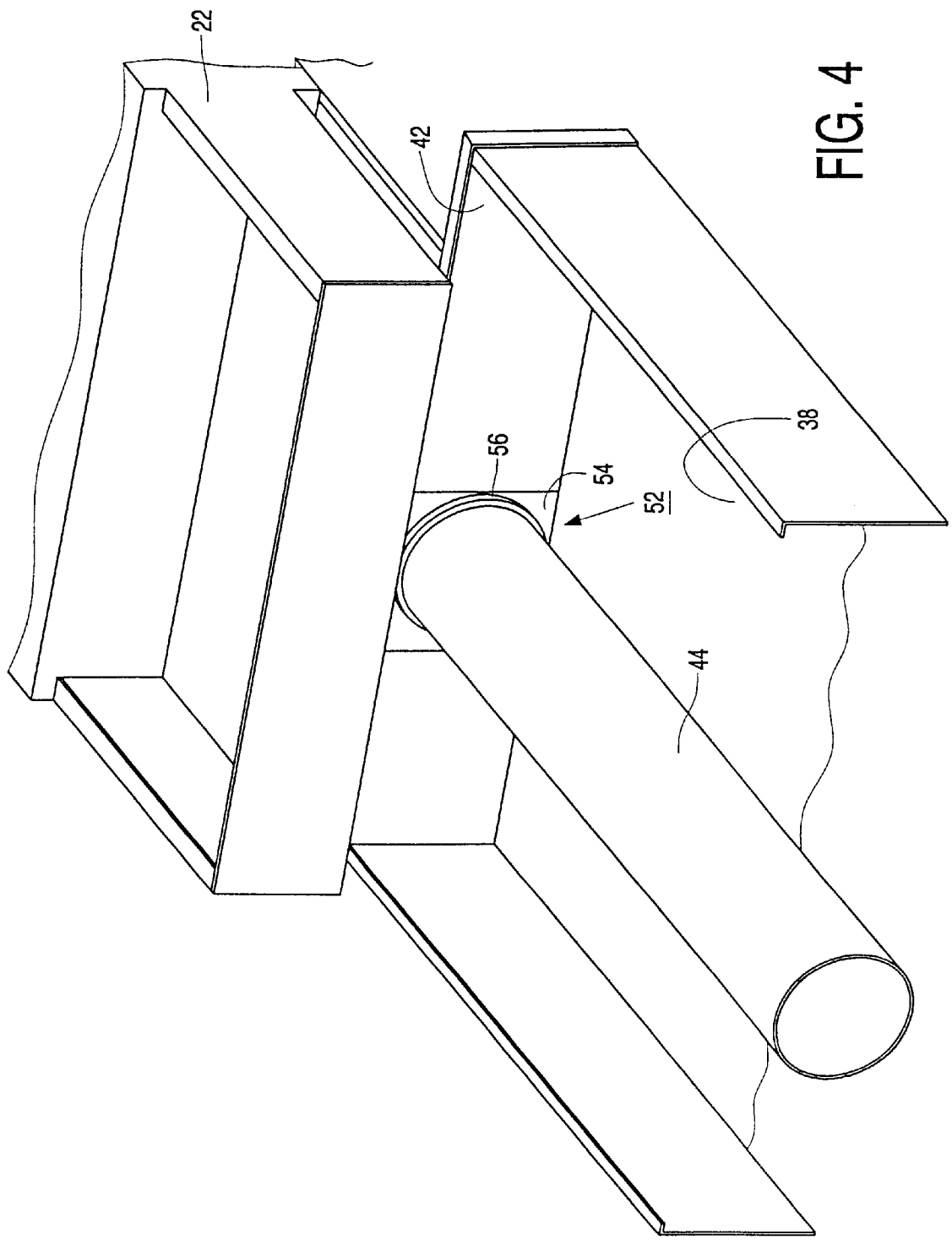

CARRIER FOR MEDICAL FACILITIES WITH A LARGE DISPLACEMENT RANGE

FIELD OF THE INVENTION

The invention relates to a carrier for medical facilities which is intended for installation in a medical treatment room and provided with a pedestal for supporting the medical facilities, wherein the pedestal is displaceable relative to the floor of the treatment room on at least one rail, and wherein the rail forms part of a first space which is separated from the medical treatment room by first cover means.

BACKGROUND INFORMATION

A carrier of this kind is known from the published German patent application No. 36 15 633 A1. The carrier disclosed therein constitutes an X-ray examination apparatus which is displaceable on a rail in the floor of the medical treatment room by way of rollers provided underneath a pedestal of the carrier. The rail is accommodated in a space in the floor, which space is covered by cover means in the form of a flexible belt which rests on the open upper side of the space. When the carrier is displaced, the belt is lifted off the floor by a mechanism which is arranged in the pedestal and in front of the rollers, after which the belt is guided along the upper side of the rollers and is lowered onto the open upper side of the space again behind the rollers. The space for the rail is thus separated from the medical treatment room, so that pollutants in front of and behind the pedestal cannot readily penetrate the space for the rail and the attendant staff in the treatment room nevertheless experiences only little nuisance from the presence of the rail and the spaces in which it is accommodated.

This known carrier, however, still has the drawback that pollutants can still penetrate the space for the rail, notably via the clearance between the rollers which is not covered by the belt since it is lifted at that area. Because of the severe requirements imposed on the cleanliness of a medical treatment room, therefore, this space must be intensively cleaned at regular intervals.

There may also be situations requiring a carrier for medical facilities which has a comparatively large range of displacement. Such a situation occurs, for example in the case of a patient table used for interventional MRI. During such an intervention a patient arranged on the table is treated and an MRI image must be formed during the execution of the treatment. The MRI apparatus is then installed in a neighboring MRI room which can be separated from the relevant medical treatment room by way of special doors. In order to transport the patient from the patient table in the medical treatment room to the table associated with the MRI apparatus, the patient table must have a comparatively large range of displacement. The rigidity and stability of the patient table must be retained during such displacement, thus necessitating a comparatively rigid pedestal having a large width in the displacement direction.

OBJECTS AND SUMMARY OF THE INVENTION

It is an object of the invention to provide a carrier of the kind set forth for which a comparatively large range of displacement is realized, the desired rigidity and stability are maintained, the displacement mechanism does not form an obstacle on the floor of the medical treatment, and easy cleaning of the carrier is achieved.

This object is achieved in that the carrier according to the invention is characterized in that the first space is connected with a second space which is covered by second cover means, which first and second space are separated from one another by a partition in which said connection is realized by an opening wherethrough a guide member for guiding the displacement of the pedestal is slidable.

The first space, provided in the floor of the treatment room, can now be used for accommodating one or more rails on which the pedestal of the carrier is displaced. This first space is adjoined by a second space which is also provided in the floor of the treatment chamber in such a manner that the second cover means are flush with the floor of the treatment room. All further components necessary for guiding the displacement of the carrier, for guiding cables, for position sensing and the like are accommodated in said second space. A guide member for guiding the displacement of the pedestal projects through the partition and hence forms a mechanical connection between the displaceable pedestal of the carrier and the second space. As a result, the guide member which is rigidly connected to the pedestal may be of comparatively large length, so that the rigidity and the stability of the pedestal, and hence of the entire carrier, can be realized by way of a comparatively small force applied at the area of the end of the guide member.

The assembly formed by the patient table and the displacement mechanism is constructed in such a manner that the first space which accommodates one or more rails does not contain other components of the displacement mechanism, so that in operating conditions this space accommodates only the guide member, being connected to the pedestal, when the patient table is in a fully or partly displaced position. The cover means of this first space, therefore, must always be provided with an opening for the passage of the link between the pedestal and the guide member, so that via this opening the space situated therebelow could be polluted from the medical treatment room. Because the first space does not accommodate any other components of the displacement mechanism, however, it can be readily cleaned.

The invention offers the additional advantage that the accessibility of the patient table is maintained, despite the facilities providing a large displacement range while maintaining the rigidity and stability. This means that the freedom of movement of attendant staff working at the patient table according to the invention is not restricted by the facilities according to the invention.

It is to be noted that in the context of the present invention the term "medical treatment" is to be understood to include also a medical examination which is performed without performing a direct therapeutic activity.

The opening in the partition in a preferred embodiment of the invention is provided with sealing means for sealing against pollutants wandering from one of the spaces to the other space. In given operating conditions it may be sufficient to have a partition with an opening which encloses the guide member comparatively tightly. This configuration already offers adequate prevention of the transfer of pollutants from one of the spaces to the other. However, it may be that this partition between the two spaces is not adequate for the described purpose. In that case a collar of an elastic material can be provided in the partition, for example a collar which tightly envelops the guide member and prevents the transfer of contaminations. Moreover, contamination of the first space from the second space (accommodating further components of the displacement mechanism) is thus also prevented.

The guide member in a further embodiment of the invention is constructed as a rod having a circular cross-section.

This shape of the guide member makes it easy to purchase it in a commercially available form and to finish it accurately, thus enabling a tight fit with the sealing; the accurately finished and hence smooth surface ensures that any wear will not be extensive.

The first space in a further embodiment is provided with two parallel rails. When these rails are mounted parallel to the longitudinal direction of the guide member, this step considerably enhances the transverse stability (i.e. the rigidity against motions in a direction transversely of the longitudinal direction of the guide member).

The two parallel rails in a further embodiment of the invention form part of respective walls of the first space. As a result, the interior of the first space will contain even fewer obstacles which could impede cleaning, so that this space can be realized in a comparatively simple manner.

The first and the second cover means in another embodiment of the invention are formed by a first and a second detachable lid, respectively. The lids of this embodiment can be manufactured in such a manner that the first lid can be readily removed by hand; this is advantageous with a view to cleaning at regular intervals. Because the second space is not contaminated from the first space, it need be opened only for maintenance and repair activities performed on the components of the displacement mechanism accommodated therein. This lid can then be constructed in the form of a lid which consists of one piece and is screwed onto the second space with a tight fit, for example via a rubber rim, so that it need be removed only by maintenance personnel assigned to this task.

The first detachable lid in another embodiment of the invention is provided with a slot for the passage of a connection piece between the guide member and the pedestal. The connection between the guide member and the pedestal is used not only to create stability, rigidity and accuracy of movement of the patient table, but also for guiding the electrical connection cables between the movable table and the environment. These cables can then be arranged in a bundle in fixed positions relative to one another, so that this bundle has a small width in the direction transversely of the direction of movement of the table. The bundle can then be arranged in the connection piece between the pedestal and the guide member; in that case this connection piece may also have a small width, so that the slot for the passage of the connection piece may be comparatively narrow.

BRIEF DESCRIPTION OF THE DRAWINGS

The invention will be described in detail hereinafter with reference to the Figures wherein corresponding reference numerals denote corresponding elements. Therein:

FIG. 4 illustrates the arrangement of the guide member and the associated seal in the displacement mechanism of a patient table according to the invention.

DETAILED DESCRIPTION OF THE PREFERRED EMBODIMENTS

Figure 1:
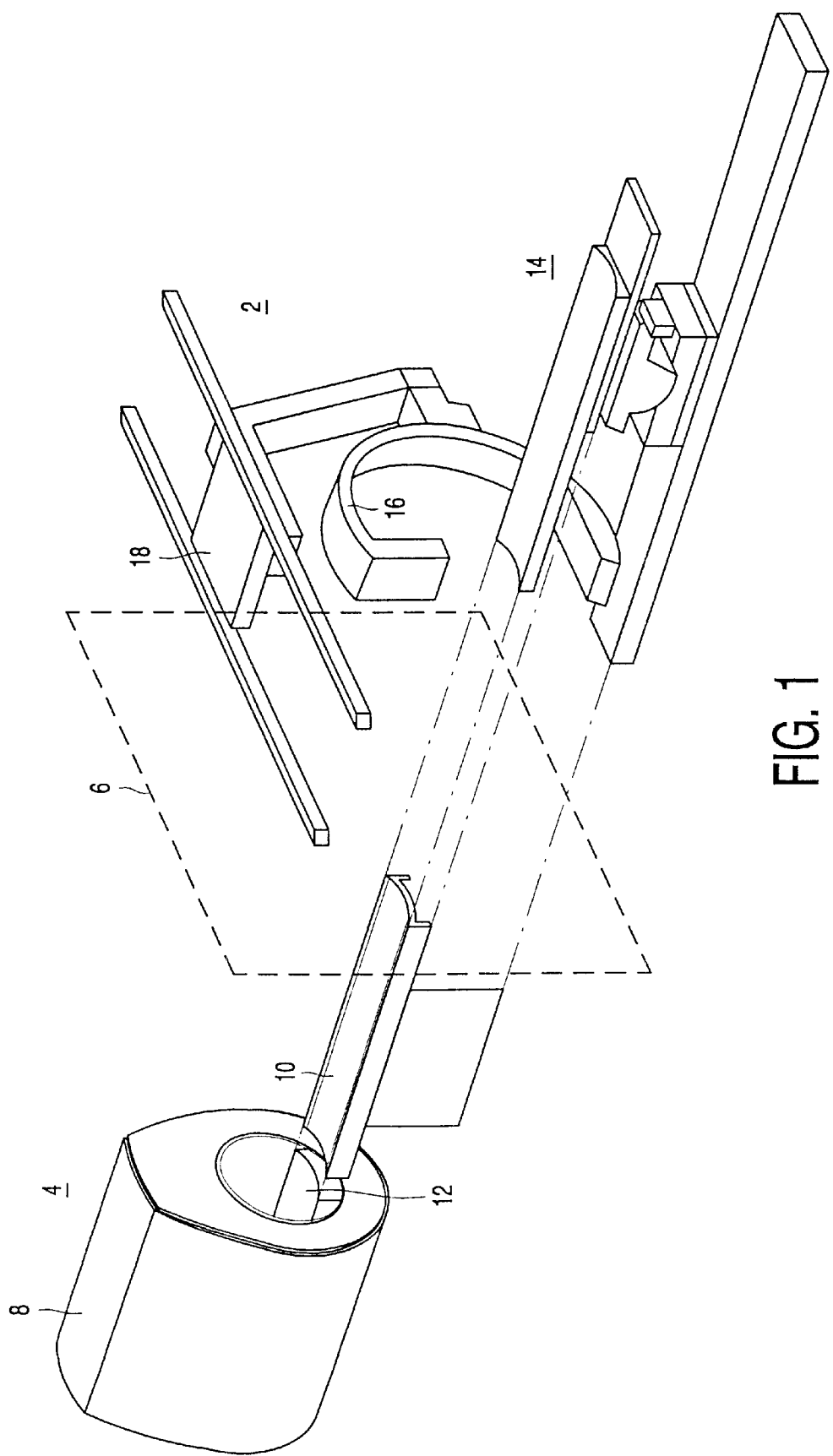
FIG. 1 shows the arrangement of a carrier according to the invention in an environment for medical treatment.

FIG. 1 is a general view of the arrangement of a carrier according to the invention in the form of a patient table in an environment for medical treatment. The environment for medical treatment in this case consists of two treatment rooms 2 and 4 that can be separated from one another. In the treatment room 4 there is installed an MRI (MRI=Magnetic Resonance Imaging) apparatus while a patient table with associated medical equipment is installed in the treatment room 2. The MRI system consists of a combination of the actual MRI apparatus 8 and an associated patient table 10 which occupies a fixed position relative to the MRI apparatus 8, so that a patient to be examined can be introduced into the bore 12 of the MRI apparatus in a controlled manner so as to form the desired magnetic resonance images.

A patient table 14 according to the invention and the associated medical equipment are installed in the treatment room 2. In this case the associated medical equipment consists of a so-called C-arm which is supported by a system 18 for supporting the C-arm, said system being secured to the ceiling (not shown) of the treatment room 2. At the ends of the C-arm there are provided an X-ray source (not shown) and an X-ray detector (not shown), for example, an image intensifier, so that the process taking place during the treatment can be followed by way of X-ray images.

The two treatment rooms 2 and 4 can be separated from one another by way of a system of doors 6 which is symbolically represented; thus, an examination or treatment can be performed in each of these rooms, without the activities in one room affecting those in the other room. For given treatments, however, it is desirable to use the two treatment rooms in a combination. This situation occurs in the case of so-called interventional MRI, that is, a treatment where an MRI image must be formed during the execution of an intervention, for example, in order to check the progress of the intervention. The system of doors 6 is in that case open, so that one combined treatment room is formed. The patient to be examined, being positioned on a table top which fits on the patient table 14 as well as on the patient table 10, can then be transferred, in principle together with the table top, from one patient table to the other. The two patient tables must then be aligned exactly relative to one another and be sufficiently rigid and stable so as to maintain this alignment, irrespective of the weight of the patient.

Because of the presence of the system of doors 6 and the space necessary around this system so as to provide access to the patient table from all sides in the case of separate treatment rooms, the distance between the patient table 6 and the patient table 10 associated with the MRI apparatus is rather large, that is, in any case so large that the usual range of displacement of approximately one meter is not sufficient for the transfer of the table top with the patient from the patient table 14 to the patient table 10 or vice versa. The described transfer of the patient requires a range of displacement of the order of magnitude of approximately three meters. With a view to the precision of the alignment of the two patient tables relative to one another, this desired large range of displacement imposes severe requirements as regards the rigidity and stability of the construction of the patient table 14 to be displaced, notably on the displacement mechanism.

Figure 2:
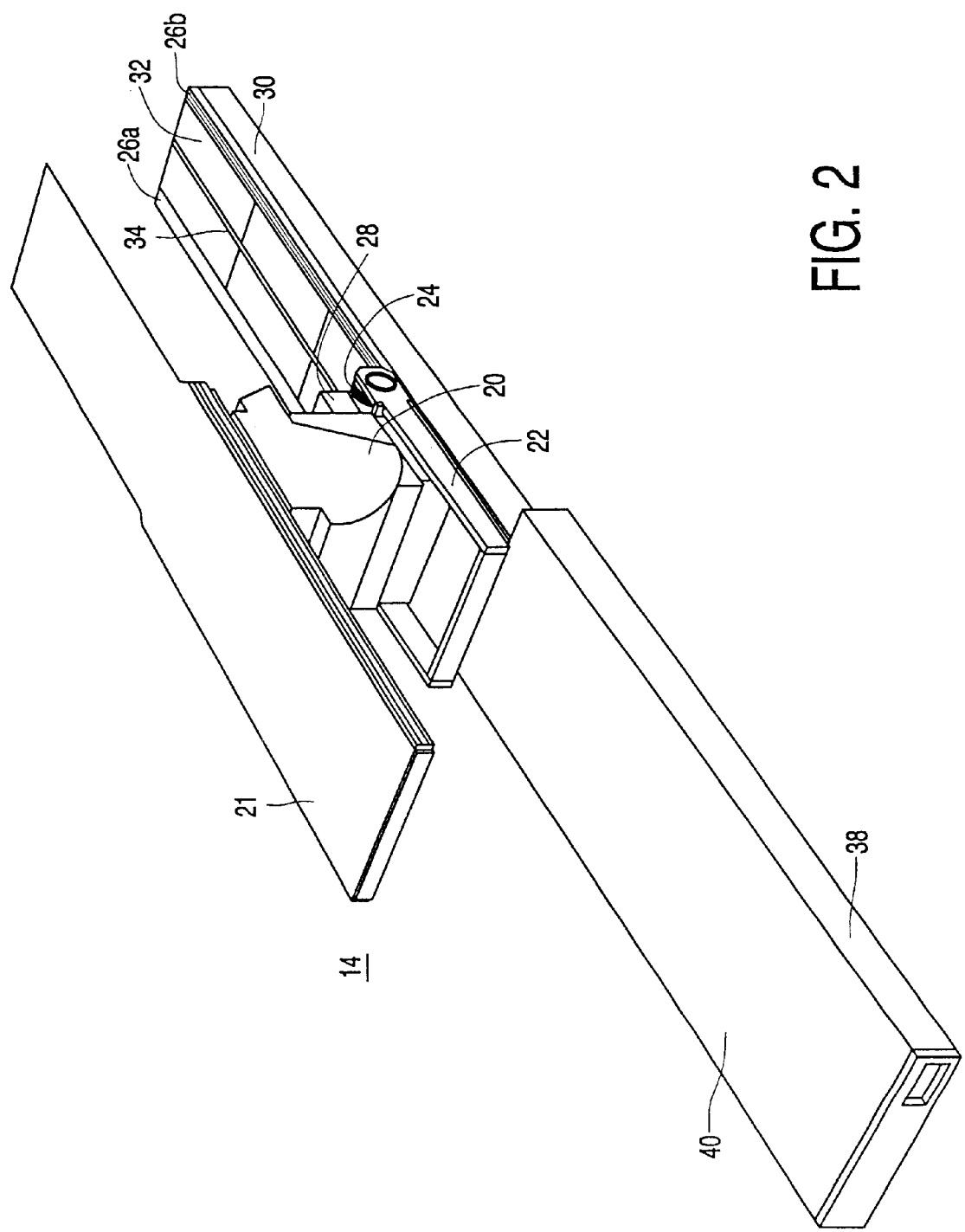
FIG. 2 is a perspective view of a carrier according to the invention in the form of a patient table.

FIG. 2 is a more detailed representation of the patient table 14 according to the invention. This patient table includes a carrier section 22 on which a table top with a patient can be arranged. The carrier section 22 is attached to a pedestal 20 and is displaceable relative thereto in a conventional manner over a distance of approximately one meter in the longitudinal direction. In order to create a larger range of displacement for the patient table 14, the pedestal 20 is arranged on a carriage 22 which is displaceable relative to the floor (not shown) of the treatment room in which the patient table is installed. The displacement of the carriage 22 takes place on rollers 24 which are mounted at two corner points of the carriage and only one of which is visible in FIG. 2. The carriage 22 is also connected to a guide member to be described with reference to the FIGS. 3 and 4 (not shown in FIG. 2).

Upon displacement of the carriage 22, the rollers 24 roll on rails 26a and 26b whose top surface is flush with the floor surface of the treatment room in which the patient table is installed. This displacement is driven by a drive unit 28 which may be provided with a drive motor and a reduction gear coupled thereto. The rails 26a and 26b form part of a first box-like space 30 which is formed in the floor of the treatment room in such a manner that the top surface of the space 30 is flush with the floor surface of the treatment room. The box-like space 30 is separated from the medical treatment room by first cover means 32. The first cover means are shaped as a manually detachable lid or a system of non-interconnected lids. At the center of the set of lids shown there is recessed a slot 34 for the passage of a connection piece (not shown) between the guide member and the pedestal 20.

Adjacent the first box-like space 30 a second box-like space 38 is formed in the floor of the treatment room, again in such a manner that the top surface of the space 38 is flush with the floor surface of the treatment room. The box-like space 38 is separated from the medical treatment room by second cover means 40. The second cover means are formed as a detachable lid 40. This lid 40 is preferably not detachable by hand but is screwed, for example, onto the walls of the box-like space 38; a rubber rim may be provided between this lid 40 and the space 38 for additional sealing. Generally speaking, the lid 40 need not be removed for the regular cleaning activities in the treatment room, but only for maintenance or repair of the parts of the displacement mechanism which are accommodated in this space.

Figure 3:
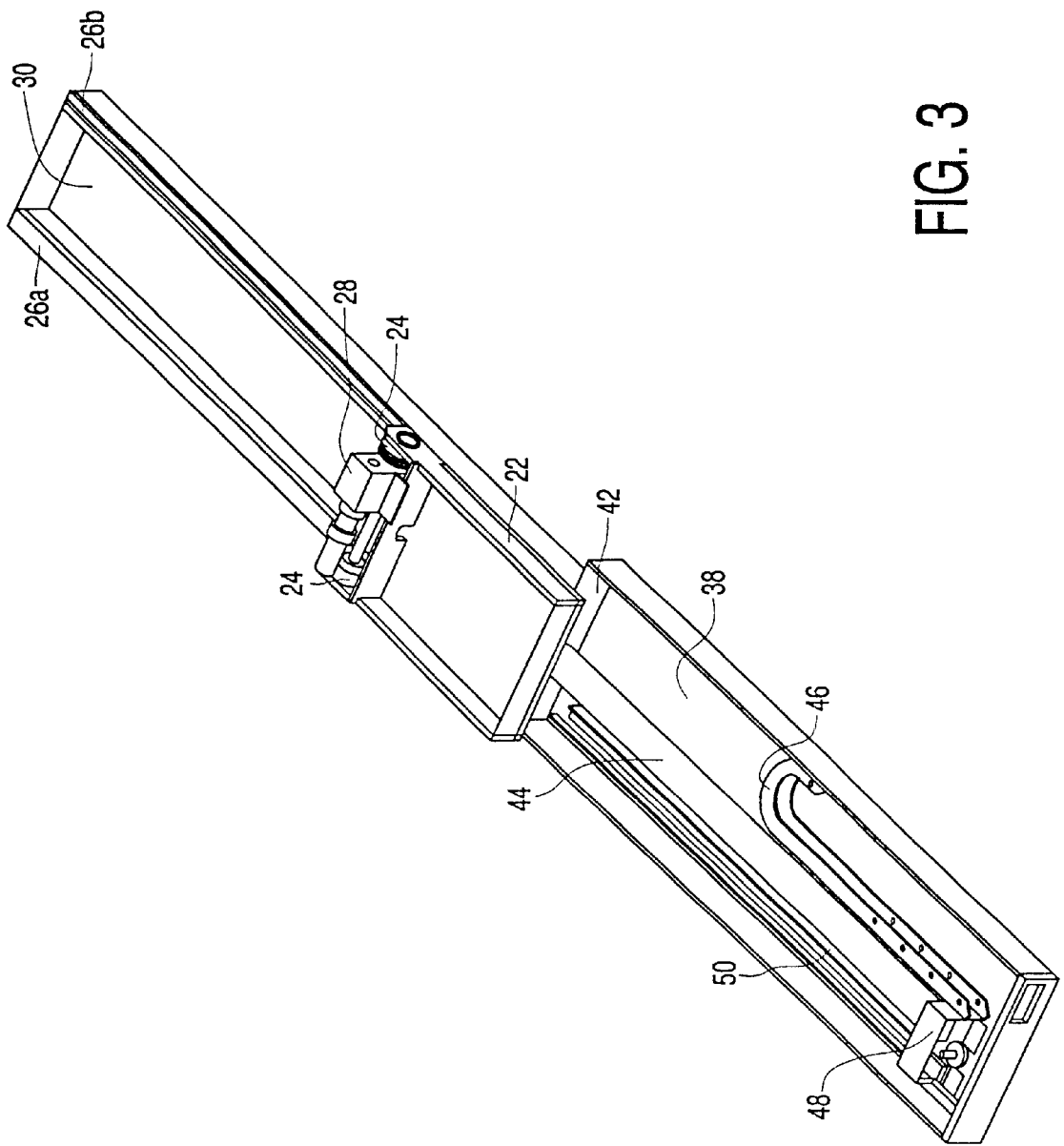
FIG. 3 is a perspective view of the displacement mechanism of a patient table according to the invention.

FIG. 3 is a more detailed representation of the displacement mechanism of the patient table 14 according to the invention. In this Figure the lids of the spaces 30 and 38 have been omitted, so that the interior of these spaces is revealed. In addition to the elements already mentioned with reference to FIG. 2, FIG. 3 also shows the partition 42 between the first space 30 and the second space 38 and also the guide member 44 for guiding the displacement of the pedestal 20. This Figure clearly shows that the rails 26a and 26b, forming part of the first space 30, constitute the walls of this space. This offers the advantage that the space 30 can be cleaned even more simply. This space thus contains only supporting elements for supporting the parts of the lid 32.

The guide member 44 is shaped as a tube having a circular cross-section. One end of the guide member 44 is connected to the carriage 22 in order to guide the displacement of the carriage. The guide member 44 is then slidable through an opening (see FIG. 4) in the partition 42. The connection between the guide member 44 and the carriage 22 has the appearance of a narrow plate which extends perpendicularly to the bottom of the carriage; the connection is situated underneath the carriage 22 and hence is not visible in FIG. 3. Upon displacement of the carriage 22 the narrow connection plate moves to and fro through the slot 34 (FIG. 2).

The cables for the electrical connections between the movable table and the environment are conducted inside said connection plate. These cables are arranged relative to one another in such a manner that the cable bundle has a small width in the direction transversely of the direction of movement of the table, so that it fits in the plate-shaped cavity. The cable bundle is guided further through the interior of the guide member 44 and emanates from this guide member 44 at the rear; the cable bundle is then introduced into a flexible cable guide 46 which moves along with the guide member 44 upon displacement, the curved part in the table guide 46 then being displaced. At the rear of the guide member 44 there is provided a guide unit 48 in which a wheel runs along a guide 50. The long length of the moment arm constituting the guide member 44 provides the stability relative to the floor and the rigidity of the patient table. The guide unit 48 may also be provided with means for determining the position of the patient table in the displacement direction, possibly in conjunction with position marking means at the area of the guide track 50.

FIG. 4 is a detailed view of the arrangement of the guide member 44 and the associated seal in the displacement mechanism of the patient table according to the invention. The lid of the space 38 has been omitted in this Figure, so that the interior of this space is visible. The Figure shows a partition 42 in which an opening 52 is provided for the guide member 44. The opening 52 is provided with a seal which is formed by a supporting plate 54 in which there is mounted a flexible ring 56. If desired, the flexible ring may be attached to a supporting ring which itself is connected to the supporting plate 54 via a further flexible ring. The advantage of such a construction consists in that the flexible ring provides suitable sealing even in the presence of slight irregularities which are due to residual surface roughness of the guide member 44, whereas displacement of the seal as a whole, despite any non-straightness of the guide member 44, is enabled by deformation of the other flexible ring which connects the supporting ring to the supporting plate.

What is claimed is:

1. A carrier for medical facilities for installation in a medical treatment room having a floor comprising:

a pedestal for supporting the medical facilities, said pedestal being displaceable relative to the floor of the medical treatment room on at least one rail which defines a part of a first space which is separated from the medical treatment room by a first cover, wherein the first space is operatively coupled to a second space which is covered by a second cover, said first and second spaces being separated from one another by a partition, said operative coupling of said first and second spaces being realized by an opening in said partition wherethrough a guide member for guiding the displacement of the pedestal is slidable.

2. The carrier for medical facilities as defined claim 1, wherein the opening in said partition comprises sealing means operatively engageable with said guide member for preventing pollutants from traversing from one of the first and second spaces to the other of the first and second spaces.

3. The carrier for medical facilities as defined by claim 1, wherein the guide member comprises a rod having a circular cross-section.

4. The carrier for medical facilities as defined by claim 1, wherein the first space comprises two parallel rails.

5. The carrier for medical facilities as defined by claim 4, wherein the two parallel rails form part of respective walls of the first space.

6. The carrier for medical facilities as defined by claim 1, wherein the first and second covers comprise respective first and second detachable lids.

7. The carrier for medical facilities as defined by claim 6, wherein the first detachable lid includes a slot for the passage of a connection piece between the guide member and the pedestal.

* * * * *